US010921276B2

(12) United States Patent
Wakabayashi

(10) Patent No.: US 10,921,276 B2
(45) Date of Patent: Feb. 16, 2021

(54) SENSOR DEVICE

(71) Applicant: ABLIC Inc., Chiba (JP)

(72) Inventor: Yuji Wakabayashi, Chiba (JP)

(73) Assignee: Ablic Inc., Chiba (JP)

( * ) Notice: Subject to any disclaimer, the term of this patent is extended or adjusted under 35 U.S.C. 154(b) by 230 days.

(21) Appl. No.: 16/191,987

(22) Filed: Nov. 15, 2018

(65) Prior Publication Data

US 2019/0154616 A1 May 23, 2019

(30) Foreign Application Priority Data

Nov. 20, 2017 (JP) ................. 2017-222522

(51) Int. Cl.
*G01N 27/22* (2006.01)
*H03K 17/955* (2006.01)
*G01R 27/26* (2006.01)
*G01B 7/06* (2006.01)
*G07D 7/026* (2016.01)

(52) U.S. Cl.
CPC ............ *G01N 27/22* (2013.01); *G01B 7/08* (2013.01); *G01R 27/2605* (2013.01); *G07D 7/026* (2013.01); *H03K 17/955* (2013.01)

(58) Field of Classification Search
CPC ............ G01P 15/125; G01P 15/131; G01P 2015/0828; G01R 27/2605; G01R 19/0061; G01R 29/24; G01D 5/24; G01D 5/2417; G01D 5/2405; G01N 27/22; G03G 15/5029; H03K 17/955
See application file for complete search history.

(56) References Cited

U.S. PATENT DOCUMENTS

| 6,538,693 B1 | 3/2003 | Kozuka | |
|---|---|---|---|
| 9,151,792 B1 * | 10/2015 | Kremin | ............. G01R 27/2605 |
| 2013/0207677 A1 * | 8/2013 | Togura | ............. G01R 27/2605 |
| | | | 324/685 |

FOREIGN PATENT DOCUMENTS

JP H09-205588 A 8/1997

\* cited by examiner

*Primary Examiner* — Lee E Rodak
(74) *Attorney, Agent, or Firm* — Brinks Gilson & Lione

(57) ABSTRACT

A sensor device includes a detection electrode opposing an external electrode, and generating a voltage corresponding to a change in capacitance; a capacitive amplifier circuit having a first capacitor and a second capacitor, and configured to detect the voltage generated in the detection electrode, and output a detection signal obtained by amplifying the voltage generated in the detection electrode based on a capacitance ratio between the first capacitor and the second capacitor; a reset switch configured to reset the voltage of the detection electrode to a reference potential; a changeover switch configured to switch the capacitive amplifier circuit between a capacitive amplifier and a voltage follower; a second changeover switch configured to disconnect the first capacitor from the capacitive amplifier circuit; and a second reset switch configured to reset a voltage of the first capacitor to the reference potential.

12 Claims, 3 Drawing Sheets

SENSOR DEVICE

RELATED APPLICATIONS

This application claims priority under 35 U.S.C. § 119 to Japanese Patent Application No. 2017-222522 filed on Nov. 20, 2017, the entire content of which is hereby incorporated by reference.

BACKGROUND OF THE INVENTION

1. Field of the Invention

The present invention relates to a sensor device.

2. Description of the Related Art

In recent years, a sensor device having a sensor has been known (refer to Japanese Patent Application Laid-open No. H09-205588, for example). In such a sensor device, a voltage generated in a photoelectric element is detected with a source follower, for example.

However, in a sensor device including, instead of the photoelectric element, a detection electrode which opposes an external electrode applied with a voltage, and in which a voltage is generated by a change in electrostatic capacitance, for example, a detection voltage which is the voltage generated in the detection electrode is minute, and hence the detection voltage is amplified in a subsequent stage of the source follower for use. In such a related-art sensor device, the detection voltage as well as a noise component is amplified. Possibility of lowering in detection accuracy remains.

The present invention has been made to provide a sensor device in which effect of noise is reduced and detection accuracy is improved.

SUMMARY OF THE INVENTION

According to one embodiment of the present invention, there is provided a sensor device including a detection electrode opposing an external electrode to which a predetermined voltage is applied, and configured to generate a voltage corresponding to a change in electrostatic capacitance; a capacitive amplifier circuit having an operational amplifier, a first capacitor, and a second capacitor connected between an output terminal and an inverting input terminal of the operational amplifier, and the first capacitor connected in series to the second capacitor, the capacitive amplifier circuit being configured to detect the voltage generated in the detection electrode and output a detection signal obtained by amplifying the voltage generated in the detection electrode based on a capacity ratio between the first capacitor and the second capacitor; a reset switch configured to reset the voltage of the detection electrode to a reference potential; a changeover switch configured to switch the capacitive amplifier circuit between a function as a capacitive amplifier and a function as a voltage follower, based on whether to establish a short circuit between the output terminal and the inverting input terminal; a second changeover switch configured to disconnect the first capacitor from the capacitive amplifier circuit for the capacitive amplifier circuit to function as the voltage follower; and a second reset switch configured to reset a voltage of the first capacitor to the reference potential according to disconnection of the first capacitor from the capacitive amplifier circuit.

According to the present invention, effects of noise can be reduced, and detection accuracy can be improved.

DETAILED DESCRIPTION OF THE PREFERRED EMBODIMENTS

Now, embodiments of the present invention are described with reference to the accompanying drawings.

First Embodiment

Figure 1:
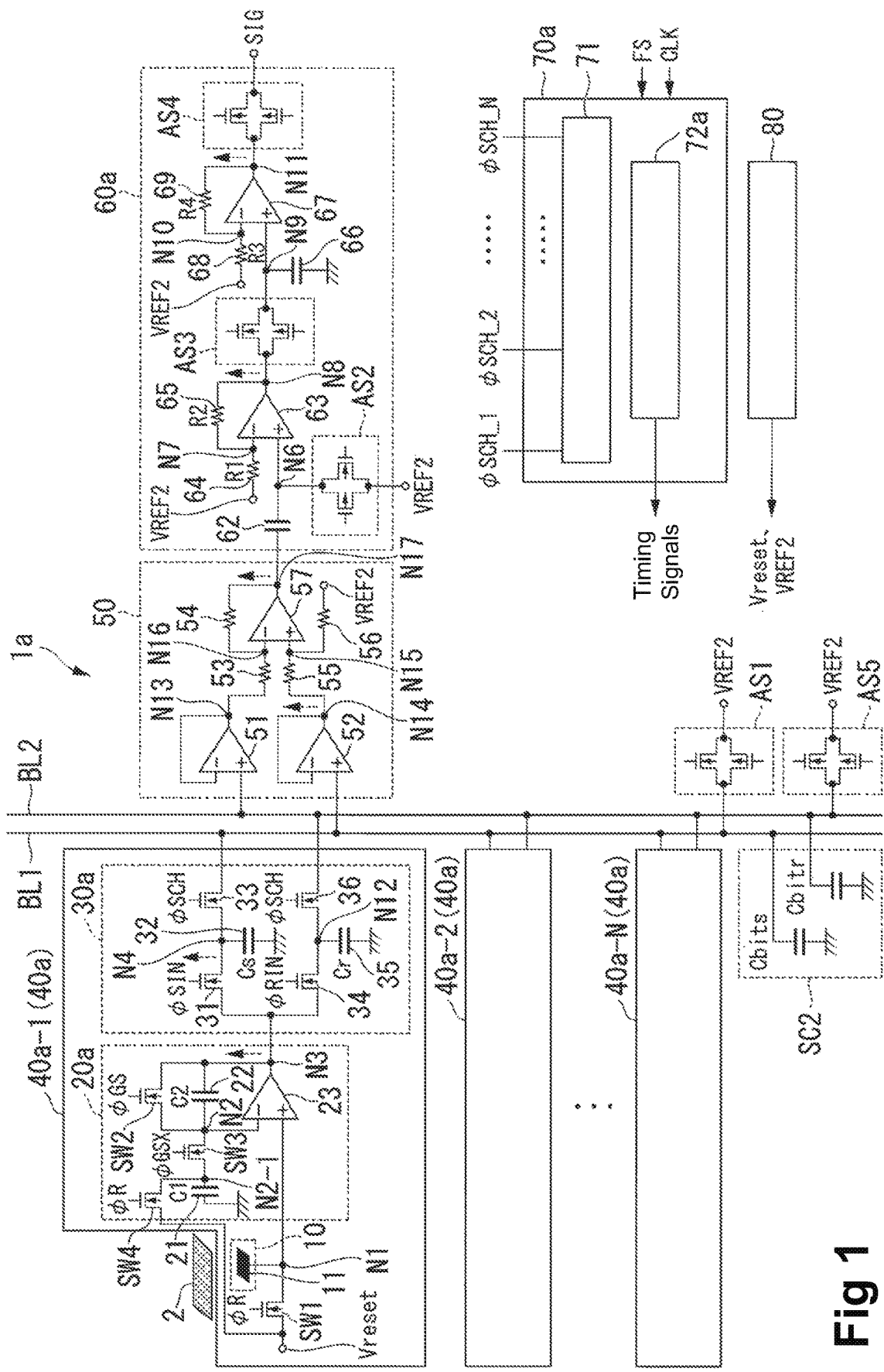
FIG. 1 is a block diagram for illustrating an example of a sensor device according to a first embodiment of the present invention.

FIG. 1 is a block diagram for illustrating an example of a sensor device 1 a according to the first embodiment of the present invention.

As illustrated in FIG. 1, the sensor device 1a includes an external electrode 2, pixel blocks (40a-1, 40a-2, . . . , 40a-N), a subtraction circuit 50, an output processing circuit 60a, a timing control circuit 70a, and a reference voltage generation circuit 80. The sensor device 1a is, for example, a line image sensor device which detects an image of a thickness of a paper sheet such as a banknote, with the use of an electrostatic capacitance. The sensor device 1a serially outputs detection voltages indicating one line of pixels from a SIG terminal. The pixel blocks (40a-1, 40a-2, . . . , 40a-N), the output processing circuit 60a, the timing control circuit 70a, and the reference voltage generation circuit 80 are formed as a semiconductor integrated circuit (large-scale integration: LSI) on one chip, for example, and the sensor device 1a includes the one-chip semiconductor integrated circuit (LSI) and the external electrode 2.

In the first embodiment, the pixel blocks (40a-1, 40a-2, . . . , 40a-N) have the same configuration, and are described as the pixel block(s) 40a when any one of the pixel blocks had in the sensor device 1a is referred to, or when the pixel blocks are not particularly distinguished from one another.

The external electrode 2 is an electrode arranged outside the pixel block 40a, and is arranged to correspond to a detection electrode 11 which is described later. The external electrode 2 is applied with a predetermined voltage V1 when the pixel block 40a detects an electric field (which corresponds to a thickness of the paper sheet) of each pixel. In the first embodiment, the external electrode 2 is formed as one electrode for all detection electrodes 11 included in the sensor device 1.

The pixel block 40a is a block which detects the electric field (thickness) of a pixel, and includes the detection electrode 11, a bit amplifier circuit 20a, a sampling circuit 30a, and a reset switch SW1.

The detection electrode 11 opposes the external electrode 2, and a voltage corresponding to a change in capacitance caused by the thickness of the paper sheet, for example, the banknote, inserted between the external electrode 2 and the detection electrode 11 is generated in the detection electrode 11. The detection electrodes 11 respectively included in the plurality of pixel blocks 40a are arranged in a line to detect pixels line by line.

The bit amplifier circuit 20a (one example of a capacitive amplifier circuit) detects the voltage generated in the detection electrode 11, and output a detection signal obtained by amplifying, based on a capacitance ratio between a capacitor 21 and a capacitor 22, the voltage generated in the detection electrode 11. Specifically, the bit amplifier circuit 20a has the capacitor 21 (the first capacitor), the capacitor 22 (the second capacitor), an operational amplifier 23, the first changeover switch SW2, the second changeover switch SW3, and the second reset switch SW4.

The capacitor 21 and the capacitor 22 are connected in series to each other via a node N2, the second changeover switch SW3, and a node N2-1. In other words, the second changeover switch SW3 is connected between the node N2 and the node N2-1. The capacitor 22 is connected between a node N3 and the node N2. The capacitor 21 is connected between the node N2-1 and a ground (GND) line (one example of a reference potential line).

The operational amplifier 23 has a non-inverting input terminal connected to the detection electrode 11 via a node N1. Moreover, the operational amplifier 23 has the capacitor 22 connected between an output terminal (node N3) and an inverting input terminal thereof, and has the capacitor 21 connected between the inverting input terminal and the reference potential line via the second changeover switch SW3. The operational amplifier 23 is connected to the capacitor 21 and the capacitor 22 as described above to function as a non-inverting amplifier circuit.

As described above, the bit amplifier circuit 20a is a capacitive non-inverting amplifier circuit (one example of a capacitive amplifier), and outputs the detection signal obtained by amplifying, by the following equation (1), the voltage generated in the detection electrode 11.

$$\text{Gain}=(C1+C2)/C2 \tag{1}$$

In the equation (1), C1 is a capacitance of the capacitor 21, and C2 is a capacitance of the capacitor 22.

In FIG. 1, the broken-line arrows indicate positive and negative directions of signals, and the bit amplifier circuit 20a (operational amplifier 23) outputs a detection signal in the positive direction.

The reset switch SW1 is an N-channel metal-oxide-semiconductor (MOS) transistor, for example, and is connected between a Vreset signal line and the node N1. The reset switch SW1 also has a gate terminal (control terminal) connected to a ΦR signal line. Here, a Vreset signal is a reference potential for initializing (resetting) the detection electrode 11. The reset switch SW1 resets the voltage of the detection electrode 11 to the reference potential Vreset.

For example, the reset switch SW1 enters an ON state (conductive state) when a ΦR signal is in a high (H) state to reset the detection electrode 11. Moreover, the reset switch SW1 enters an OFF state (non-conductive state) when the ΦR signal is in a low (L) state.

In the following description, the above-mentioned N-channel MOS transistor is referred to as the "NMOS transistor".

The first changeover switch SW2 switches the bit amplifier circuit 20a between a function as a capacitive amplifier and a function as a voltage follower. The first changeover switch SW2 is an NMOS transistor, for example, and is connected between the output terminal (node N3) of the operational amplifier 23 and the inverting input terminal (node N2) of the operational amplifier 23. An ON state of the first changeover switch SW2 causes the bit amplifier circuit 20a to function as the voltage follower. In other words, the first changeover switch SW2 switches the bit amplifier circuit 20a between the function as the capacitive amplifier and the function as the voltage follower in response to a ΦGS signal, based on whether to establish a short circuit between the output terminal and the inverting input terminal of the operational amplifier 23.

For example, an H state of the ΦGS signal turns on the first changeover switch SW2 to cause the bit amplifier circuit 20a to function as the voltage follower. Moreover, an L state of the ΦGS signal turns off the first changeover switch to cause the bit amplifier circuit 20a to function as the capacitive amplifier.

The second changeover switch SW3 switches between making and breaking the connection between the capacitor 21 and the inverting input terminal of the operational amplifier 23. The second changeover switch SW3 is an NMOS transistor, for example, and is connected between the capacitor 21 and the inverting input terminal of the operational amplifier 23. An ON state of the second changeover switch SW3 makes the connection between the capacitor 21 and the inverting input terminal of the operational amplifier 23. Moreover, an OFF state of the second changeover switch SW3 breaks the connection between the capacitor 21 and the inverting input terminal of the operational amplifier 23. In other words, the OFF state of the second changeover switch SW3 disconnects the capacitor 21 from the operational amplifier 23.

A magnitude of parasitic capacitance of the first changeover switch SW2 and a magnitude of parasitic capacitance of the second changeover switch SW3 may be associated with each other. An example of the association between the magnitudes of parasitic capacitance is a case in which the magnitude of parasitic capacitance of the first changeover switch SW2 and the magnitude of parasitic capacitance of the second changeover switch SW3 are the same. As an example, the first changeover switch SW2 and the second changeover switch SW3 may be switches of the same type or the same size.

The second reset switch SW4 is an NMOS transistor, for example, and is connected between the Vreset signal line and the node N2-1. Moreover, the second reset switch SW4 has a gate terminal (control terminal) connected to the ΦR signal line. The second reset switch SW4 resets a voltage of the capacitor 21 to the reference potential Vreset.

For example, the high (H) state of the ΦR signal turns on the second reset switch SW4 to reset the voltage of the capacitor 21. Moreover, the low (L) state of the ΦR signal turns off the second reset switch SW4.

The sampling circuit 30a is a sample-and-hold circuit configured to sample and hold the detection signal and a reference signal provided from the bit amplifier circuit 20a by sampling and holding the detection signal and the reference signal. The sampling circuit 30a has NMOS transistors (31 and 33), a capacitor 32, NMOS transistors (34 and 36), and a capacitor 35.

The NMOS transistor 31 is connected between the node N3 and a node N4, and has a gate terminal connected to a Φ SIN signal line. An H state of a Φ SIN signal turns on the NMOS transistor 31 to sample the detection signal provided from the bit amplifier circuit 20a, and hold the detection signal in the capacitor 32. Moreover, an L state of the Φ SIN signal turns off the NMOS transistor 31 to stop sampling the detection signal provided from the bit amplifier circuit 20a.

The capacitor 32 is connected between the node N4 and a GND line to hold the sampled detection signal.

The NMOS transistor 33 is connected between the node N4 and a common signal line BL1, and has a gate terminal connected to a ΦSCH signal line. An H state of a ΦSCH signal turns on the NMOS transistor 33 to output the detection signal held by the sampling circuit 30a (capacitor 32) to the common signal line BL1. Moreover, an L state of the ΦSCH signal turns off the NMOS transistor 33 to stop the output to the common signal line BL1.

The NMOS transistor 34 is connected between the node N3 and a node N12, and has a gate terminal connected to a ΦIN signal line. An H state to of a ΦIN signal turns on the NMOS transistor 34 to sample the detection signal provided from the bit amplifier circuit 20a, and hold the detection signal in the capacitor 35. Moreover, an OFF state of the ΦIN signal turns off the NMOS transistor 34 to stop sampling the detection signal provided from the bit amplifier circuit 20a.

The capacitor 35 is connected between the node N12 and a GND line to hold the sampled detection signal.

The NMOS transistor 36 is connected between the node N12 and a common signal line BL2, and has a gate terminal connected to a ΦSCH signal line. An H state of a ΦSCH signal turns on the NMOS transistor 36 to output the detection signal held by the sampling circuit 30a (capacitor 35) to the common signal line BL2. Moreover, an L state of the ΦSCH signal turns off the NMOS transistor 36 to stop the output to the common signal line BL2.

The sampling circuit 30a reduces an offset of the bit amplifier circuit 20a by sampling and holding the reference signal. The "reference signal" as used herein refers to an output signal from the bit amplifier circuit 20a after the voltage of the detection electrode 11 is reset to the reference potential Vreset by the reset switch SW1 and the function of the bit amplifier circuit 20a is switched from the voltage follower to the capacitive amplifier by the first changeover switch SW2, and further after the connection between the capacitor 21 and the inverting input terminal of the operational amplifier 23 is broken by the second changeover switch SW3, but before the predetermined voltage is applied to the external electrode 2. The reference signal contains a noise generated in the switching of the function from the voltage follower to the capacitive amplifier by the ΦGS signal to the first changeover switch SW2, and a noise generated in the break of the connection between the capacitor 21 and the inverting input terminal of the operational amplifier 23 by a ΦGSX signal to the second changeover switch SW3.

To the common signal line BL1 and the common signal line BL2, the sampling circuit 30a of each of the pixel blocks (40a-1, 40a-2, . . . , 40a-N) is connected. The sampling circuits 30a of the respective pixel blocks 40a each output the detection signal one pixel at a time to the common signal line BL1 and output the reference signal one pixel at a time to the common signal line BL2, in response to ΦSCH signals (ΦSCH_1 signal, ΦSCH_2 signal, . . . , ΦSCH_N signal) respectively corresponding to the pixel blocks 40a. Moreover, the common signal line BL1 and the common signal line BL2 have a parasitic capacitance SC2.

A gain of the detection signal in the sampling circuit 30a is expressed by the following equation (2).

$$\text{Gain} = Cs/(Cs + C\text{bits}) \qquad (2)$$

In the equation (2), Cs is a capacitance of the capacitor 32, and Cbits is a parasitic capacitance of the common signal line BL1.

A gain of the reference signal in the sampling circuit 30a is expressed by the following equation (3).

$$\text{Gain} = Cr/(Cr + C\text{bitr}) \qquad (3)$$

In the equation (3), Cr is a capacitance of the capacitor 35, and Cbitr is a parasitic capacitance of the common signal line BL2.

Moreover, to the common signal line BL1, an analog switch AS1 is connected.

The analog switch AS1 is connected between the common signal line BL1 and a VREF2 signal line. The analog switch AS1 is formed by pairing an NMOS transistor and a P-channel MOS transistor (PMOS transistor) to each other, and establishes bidirectional conduction between the common signal line BL1 and the VREF2 signal line in response to a control signal. When the control signal turns on the analog switch AS1, the common signal line BL1 is set to a reference potential VREF2.

Moreover, to the common signal line BL2, an analog switch AS5 is connected.

The analog switch AS5 has a configuration similar to that of the analog switch AS1 described above, and is connected between the common signal line BL2 and a VREF2 signal line. The analog switch AS5 establishes bidirectional conduction between the common signal line BL2 and the VREF2 signal line in response to a control signal. When the control signal turns on the analog switch AS5, the common signal line BL2 is set to a reference potential VREF2.

The subtraction circuit 50 generates a difference between the reference signal and the detection signal which are held by the sampling circuit 30a. The subtraction circuit 50 generates a differential signal obtained by subtracting the reference signal from the detection signal. The subtraction circuit 50 has operational amplifiers (51, 52, and 57) and resistors (53 to 56).

The operational amplifier 51 has a non-inverting input terminal connected to the common signal line BL2, and an output terminal (node N13) connected to an inverting input terminal thereof. The operational amplifier 51 functions as a voltage follower having unity gain (a gain of 1), and outputs a signal equal to the reference signal acquired via the common signal line BL2 to the output terminal (node N13).

The operational amplifier 52 has a non-inverting input terminal connected to the common signal line BL1, and an output terminal (node N14) connected to an inverting input terminal thereof. The operational amplifier 52 functions as a voltage follower having unity gain (a gain of 1), and outputs a signal equal to the detection signal acquired via the common signal line BL1 to the output terminal (node N14).

The resistor 53 is connected between the node N13 and a node N16, and the resistor 54 is connected between the node N16 and a node N17. Moreover, the resistor 55 is connected between the node N14 and a node N15, and the resistor 56 is connected between the node N15 and the VREF2 signal line.

The operational amplifier 57 has a non-inverting input terminal connected to the node N15, an inverting input terminal connected to the node N16, and an output terminal connected to the node N17. Here, the resistor 53 to the resistor 56 and the operational amplifier 57 form the subtraction circuit which subtracts the reference signal from the detection signal. The operational amplifier 57 outputs, to the output terminal (node N17), the differential signal obtained by subtracting the reference signal acquired via the common signal line BL2 from the detection signal acquired via the common signal line BL1 as the detection signal from which the offset of the bit amplifier circuit 20a is removed.

The output processing circuit 60a acquires the differential signals of the subtraction circuits 50 as the detection signals of the pixel blocks 40a one bit (one pixel) at a time, amplifies the acquired detection signals, and outputs the amplified detection signals from the SIG terminal. The output processing circuit 60a acquires the detection signals from the pixel blocks 40a via the common signal line BL1 one bit (one pixel) at a time, amplifies the acquired detection signals, and outputs the amplified detection signals from the SIG terminal. The output processing circuit 60a has operational amplifiers (63 and 67), capacitors (62 and 66), resistors (64, 65, 68, and 69), and analog switches (AS2 to AS4).

The capacitor 62 is connected between the node N17 and a node N6 to transfer the detection signal provided from the operational amplifier 57 to the node N6. The capacitor 62 converts the detection signal into a signal with reference to the reference potential VREF2 by transferring the detection signal to the node N6 that has been set to the reference potential VREF2 by the analog switch AS2 to be described below.

The analog switch AS2 has a configuration similar to that of the analog switch AS1 described above, and is connected between the node N6 and the VREF2 signal line. The analog switch AS2 establishes conduction between the node N6 and the VREF2 signal line in response to a control signal, and sets the node N6 to the reference potential VREF2.

The operational amplifier 63 has a non-inverting input terminal connected to the node N6, an inverting input terminal connected to a node N7, and an output terminal connected to a node N8. Moreover, the resistor 64 and the resistor 65 are connected in series to each other between the node N8 and the VREF2 signal line, and the operational amplifier 63 functions as a non-inverting amplifier circuit which amplifies a signal at the node N6 based on a resistance ratio between the resistor 64 and the resistor 65. In other words, the operational amplifier 63 outputs the detection signal that has been amplified by the following equation (4) to the node N8.

$$\text{Gain}=(R1+R2)/R1 \quad (4)$$

In the equation (4), R1 is a resistance of the resistor 64, and R2 is a resistance of the resistor 65.

The analog switch AS3 has a configuration similar to that of the analog switch AS1 described above, and is connected between the node N8 and a node N9. The analog switch AS3 establishes conduction between the node N8 and the node N9 in response to a control signal so that the capacitor 66 holds the detection signal that has been amplified by the operational amplifier 63.

The capacitor 66 is connected between the node N9 and the GND line to hold the detection signal that has been amplified by the operational amplifier 63. The analog switch AS3 and the capacitor 66 form a sample-and-hold circuit.

The operational amplifier 67 has a non-inverting input terminal connected to the node N9, an inverting input terminal connected to a node N10, and an output terminal connected to a node N11. Moreover, the resistor 68 and the resistor 69 are connected in series to each other between the node N11 and the VREF2 signal line, and the operational amplifier 67 functions as a non-inverting amplifier circuit which amplifies a signal at the node N9 based on a resistance ratio between the resistor 68 and the resistor 69. In other words, the operational amplifier 67 outputs to the node N11 the detection signal obtained by further amplifying the signal at the node N9 held in the capacitor 66, by the following equation (5).

$$\text{Gain}=(R3+R4)/R3 \quad (5)$$

In the equation (5), R3 is a resistance of the resistor 68, and R4 is a resistance of the resistor 69.

The analog switch AS4 has a configuration similar to that of the analog switch AS1 described above, and is connected between the node N11 and the SIG terminal. The analog switch AS4 establishes conduction between the node N11 and the SIG terminal in response to a control signal, and outputs the detection signal that has been amplified by the operational amplifier 67 to the SIG terminal.

The timing control circuit 70a generates various timing signals for controlling the sensor device 1a. For example, the timing control circuit 70a generates, for the pixel blocks 40a, various timing signals for detecting the voltage generated in the detection electrode 11 based on a frame start (FS) signal and a clock (CLK) signal, for example. Moreover, the timing control circuit 70a generates, based on the FS signal, for example, the ΦSCH signals (ΦSCH_1 signal, ΦSCH_2 signal, . . . , ΦSCH_N signal) for outputting the detection signals from the pixel blocks 40a to the common signal line BL1. The timing control circuit 70a has a shift resistor 71 and a timing signal generation circuit 72a.

The shift resistor 71 is shifted by the CLK signal and sequentially outputs H states each having a predetermined pulse width as the ΦSCH signals (ΦSCH_1 signal, ΦSCH_2 signal, . . . , ΦSCH_N signal) for providing the detection signals from the pixel blocks 40a to the common signal line BL1. In response to the output ΦSCH signals (ΦSCH_1 signal, ΦSCH_2 signal, . . . , ΦSCH_N signal), the detection signals are provided from the pixel blocks 40a to the common signal line BL1 one pixel (one bit) at a time.

The timing signal generation circuit 72a generates the ΦR signal, the Φ SIN signal, a ΦI signal, and the control signals for controlling the various analog switches (AS1 to AS5), for example, and output the generated signals to the components.

The timing control circuit 70a generates the various timing signals to perform the following timing control (A) to (C), for example.

(A) Resetting the voltage of the detection electrode 11 to the reference potential Vreset by the reset switch SW1. Breaking the connection between the capacitor 21 and the inverting input terminal of the operational amplifier 23 by the second changeover switch SW3. Resetting the voltage of the capacitor 21 to the reference potential Vreset by the second reset switch SW4. Setting the bit amplifier circuit 20a to function as the voltage follower by the first changeover switch SW2.

In other words, the connection between the capacitor 21 and the inverting input terminal of the operational amplifier 23 is disconnected for the bit amplifier circuit 20a to function as the voltage follower. Moreover, the voltage of the capacitor 21 is reset to the reference potential Vreset after disconnection of the capacitor 21 from the operational amplifier 23.

(B) Releasing from, by the reset switch SW1, a state in which the voltage of the detection electrode 11 is reset to the reference potential Vreset. Releasing from, by the second reset switch SW4, a state in which the voltage of the capacitor 21 is reset to the reference potential Vreset. Making connection between the capacitor 21 and the inverting input terminal of the operational amplifier 23 by the second changeover switch SW3. Holding the reference signal by the sampling circuit 30a after the function as the voltage follower is released by the first changeover switch SW2.

(C) Releasing the function as the voltage follower by the first changeover switch SW2, making connection between the capacitor 21 and the inverting input terminal of the operational amplifier 23 by the second changeover switch SW3, and holding the detection signal in the sampling circuit 30a after elapse of the predetermined period TR1 since the application of the predetermined voltage to the external electrode 2.

The timing control circuit 70a has a shift resistor 71 and a timing signal generation circuit 72a.

The timing signal generation circuit 72a generates the ΦR signal, the ΦGS signal, the ΦRIN signal, the Φ SIN signal, a ΦI signal, and control signals for controlling the various analog switches (AS1 to AS5), for example, and output the generated signals to the components.

The reference voltage generation circuit 80 generates reference potentials (reference voltages) for various analog circuits used in the sensor device 1a, and supplies the generated reference potentials to the components. The reference voltage generation circuit 80 generates reference potentials, such as the reference potential VREF2 and the reference potential Vreset, for example.

Next, operation of the sensor device 1a according to the first embodiment is described with reference to the accompanying drawings.

Figure 2:
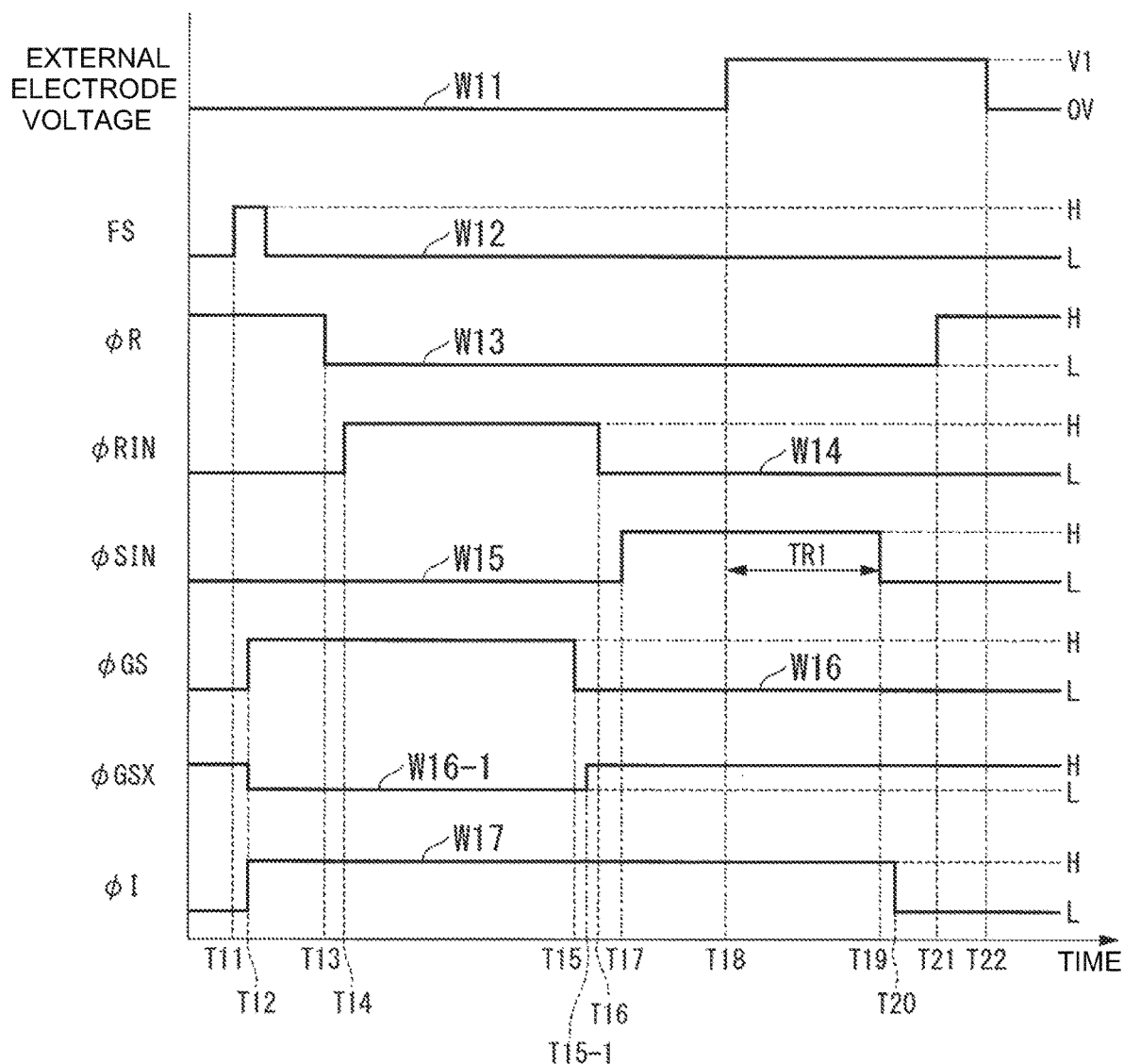
FIG. 2 is a timing chart for showing an example of operation of the sensor device according to the first embodiment.

FIG. 2 is a timing chart for showing an example of the operation of the sensor device 1a according to the first embodiment.

In the example shown in FIG. 2, a description is given of operation of the sensor device 1a until the voltage of the detection electrode 11 is detected and the detected detection signal is held in the sampling circuit 30a.

In FIG. 2, a waveform W11 indicates a waveform of the voltage of the external electrode 2 (external electrode voltage). Moreover, a waveform W12 to a waveform W17 indicate, in order from above, a logic state of the FS signal, a logic state of the ΦR signal, a logic state of the ΦRIN signal, a logic state of the Φ SIN signal, a logic state of the ΦGS signal, a logic state of the ΦGSX signal, and a logic state of the ΦI signal. In FIG. 2, the horizontal axis indicates time. Moreover, the ΦI signal is a control signal for operating the bit amplifier circuit 20a (for example, control signal for turning ON/OFF a bias current of the operational amplifier 23).

As shown in FIG. 2, it is assumed that the timing signal generation circuit 72a sets, as an initial state, the ΦR signal to the H state, and the Φ SIN signal and the ΦI signal to the L state. In this condition, the reset switch SW1 and the second reset switch SW4 enter the ON states to reset the voltage of the detection electrode 11 and the voltage of the capacitor 21 to the reference potential Vreset, respectively. Under this condition, when the FS signal is set to a H state at time T11, the timing signal generation circuit 72a sets the ΦI signal and the ΦGS signal to the H state, and the ΦGSX signal to a L state at time T12 (see the waveform W17, the waveform W16, and the waveform 16-1). In this manner, the timing signal generation circuit 72a turns off the second changeover switch SW3 to disconnect the capacitor 21 from the operational amplifier 23 and start operation of the operational amplifier 23, and turns on the first changeover switch SW2 to set the bit amplifier circuit 20a to function as the voltage follower.

Next, when the timing signal generation circuit 72a sets the ΦR signal to the L state at time T13 (see the waveform W13), each of the reset switch SW1 and the second reset switch SW4 turns off.

Next, when the timing signal generation circuit 72a sets the ΦIN signal to the H state at time T14 (see the waveform W14), the NMOS transistor 34 of the sampling circuit 30a enters the ON state to accumulate an output signal (reference signal) of the bit amplifier circuit 20a in the capacitor 35.

Next, the timing signal generation circuit 72a sets the ΦGS signal to the L state at time T15 (see the waveform W16), sets the ΦGSX signal to a H state at time T15-1 (see the waveform W16-1), and sets the ΦIN signal to the L state at time T16 (see the waveform W14). As a result, the NMOS transistor 34 turns off to complete the sampling and holding in response to the ΦIN signal, and hold, in the capacitor 35, the reference signal containing the noise generated by each transition from the H state to the L state of the ΦR signal and the ΦGS signal, and the noise generated by transition from the L state to the H state of the ΦGSX signal. Here, the reference signals of all pixels of one line of the pixel block 40a-1, the pixel block 40a-2, . . . , the pixel block 40a-N are held in the respective sampling circuits 30a.

Moreover, setting of the ΦGS signal to the L state turns off the first changeover switch SW2, and a path leading from the node N3 to the node N2 via the first changeover switch SW2, that is, a path bypassing the capacitor 22, is blocked. Moreover, setting of the ΦGSX signal to the H state turns on the second changeover switch SW3, and the capacitor 21 is connected to the inverting input terminal of the operational amplifier 23. Through the operation of those two switches, the bit amplifier circuit 20a functions as the capacitive amplifier.

Next, when the timing signal generation circuit 72a sets the Φ SIN signal to a H state (see the waveform W15) at time T17, the NMOS transistor 31 of the sampling circuit 30a enters an ON state to accumulate the output signal of the bit amplifier circuit 20a in the capacitor 32.

Next, when the predetermined voltage V1 is applied to the external electrode 2 at time T18 (see the waveform W11), a voltage corresponding to a change in capacitance caused by the thickness of the paper sheet is generated in the detection electrode 11. The bit amplifier circuit 20a outputs the detection signal obtained by amplifying the voltage generated in the detection electrode 11 with the gain of the equation (1) described above to a node N3, and the amplified detection signal is accumulated in the capacitor 32 via the NMOS transistor 31.

Next, at time T19, the timing signal generation circuit 72a sets the Φ SIN signal to the L state (see the waveform W15) after the predetermined period TR1 has elapsed since the application of the predetermined voltage V1 to the external electrode 2. Here, the predetermined period TR1 is a period enough to accumulate the detection signal that has been amplified by the operational amplifier 23 in the capacitor 32 of the sampling circuit 30a. Setting of the Φ SIN signal to the L state turns off the NMOS transistor 31 to complete the sampling and holding in response to the Φ SIN signal and hold the amplified detection signal in the capacitor 32. Here, the detection signals of all pixels of one line of the pixel block 40a-1, the pixel block 40a-2, . . . , the pixel block 40a-N are held in the respective sampling circuits 30a.

As described above, the sampling circuit 30a holds the reference signal after the voltage of the detection electrode 11 is reset to the reference potential Vreset by the reset switch SW1, and the bit amplifier circuit 20a is set to function as the voltage follower by the first changeover switch SW2, and further a state in which the voltage of the detection electrode 11 is reset to the reference potential Vreset is released by the reset switch SW1, and the function as the voltage follower is released by the first changeover switch SW2. Then, the sampling circuit 30a holds the detection signal after the function as the voltage follower is released by the first changeover switch SW2, and the predetermined period elapses since the application of the predetermined voltage to the external electrode 2.

Next, at time T20, the timing signal generation circuit 72a sets the ΦI signal to the L state to stop the operation of the operational amplifier 23.

Moreover, at time T21, the timing signal generation circuit 72a sets the ΦR signal to the H state such that the reset switch SW1 enters the ON state to reset the detection electrode 11 to the reference potential Vreset.

Next, at time T22, the application of the predetermined voltage V1 to the external electrode 2 is stopped, and the voltage of the external electrode 2 (external electrode voltage) becomes 0 V, for example (see the waveform W11).

Next, the operation for generation of the difference between the detection signal and the reference signal held in the sampling circuit 30a and for serial output of the difference as the detection signal from which the offset is removed is described with reference to FIG. 1.

After holding the detection signal and the reference signal in the sampling circuit 30a, the timing signal generation circuit 72a first turns on the analog switch AS1, the analog switch AS5, and the analog switch AS2 to set the common signal line BL1, the common signal line BL2, and a node N6 to the reference potential VREF2.

Next, after the timing signal generation circuit 72a turns off the analog switch AS1, the analog switch AS5, and the analog switch AS2, the shift resistor 71 sets a ΦSCH_1 signal to a H state. As a result, the timing signal generation circuit 72a turns on the NMOS transistor 33 of the pixel block 40a-1 to output the detection signal held in the sampling circuit 30a to the common signal line BL1, and turns on the NMOS transistor 36 of the pixel block 40a-1 to output the reference signal held in the sampling circuit 30a to the common signal line BL2.

Next, the subtraction circuit 50 generates the differential signal obtained by subtracting the reference signal from the detection signal, and outputs the differential signal to the node N17.

Next, the output processing circuit 60a acquires the differential signal of the subtraction circuit 50 as the detection signal, amplifies the acquired detection signal, and outputs the amplified detection signal from the SIG terminal.

Next, the timing control circuit 70a executes processing similar to that for the pixel block 40a-1 on the pixel block 40a-2. In this case, the shift resistor 71 is shifted by the CLK signal to set a ΦSCH_2 signal to a H state such that the output processing circuit 60a outputs a detection signal of the pixel block 40a-2 as a detection voltage of one pixel to the SIG terminal.

The timing control circuit 70a repeats such processing until a detection signal of the pixel block 40a-N is provided to the SIG terminal.

As described above, the sensor device 1a according to the first embodiment has the detection electrode 11, the bit amplifier circuit 20a (capacitive amplifier circuit), the reset switch SW1, the first changeover switch SW2, the second changeover switch SW3, the second reset switch SW4, the sampling circuit 30a, and the subtraction circuit 50. The detection electrode 11 opposes the external electrode 2 to which the predetermined voltage V1 is applied, and the voltage corresponding to the change in capacitance is generated therein. The bit amplifier circuit 20a has the capacitor 21 (first capacitor) and the capacitor 22 (second capacitor) connected in series to each other to detect the voltage generated in the detection electrode 11, and output the detection signal obtained by amplifying, based on the capacitance ratio between the capacitor 21 and the capacitor 22, the voltage generated in the detection electrode 11. The reset switch SW1 resets the voltage of the detection electrode 11 to the reference potential Vreset. The first changeover switch SW2 switches the bit amplifier circuit 20a between the function as the capacitive amplifier and the function as the voltage follower. The second changeover switch SW3 disconnects the capacitor 21 from the operational amplifier 23 for the bit amplifier circuit 20a to function as the capacitive amplifier. The second reset switch SW4 supplies the reference potential Vreset to the capacitor 21 to reset the voltage of the capacitor 21 to the reference potential Vreset when the capacitor 21 is disconnected from the operational amplifier 23. The sampling circuit 30a holds the reference signal and the detection signal under the state in which the predetermined voltage is applied to the external electrode 2 by sampling and holding the reference signal and the detection signal. Here, the reference signal is the output signal from the bit amplifier circuit 20a which is set to function as the voltage follower by the first changeover switch SW2 after the voltage of the detection electrode 11 is reset to the reference potential Vreset by the reset switch SW1 and before the predetermined voltage is applied to the external electrode 2. The subtraction circuit 50 generates the difference between the reference signal and the detection signal held in the sampling circuit 30a.

As a result, the sensor device 1a according to the first embodiment amplifies the voltage generated in the detection electrode 11 by the bit amplifier circuit 20a, and outputs the amplified voltage as the detection signal, with the result that the effects of noise, for example, thermal noise can be reduced in processing in a subsequent stage of the bit amplifier circuit 20a, for example. Accordingly, the sensor device 1a according to the first embodiment can improve detection accuracy.

Moreover, in a standard semiconductor process, a capacitor can be implemented with a size (area) that is smaller than that of a resistive element. The sensor device 1a according to the first embodiment employs the capacitive amplifier, and hence can reduce a process cost.

Moreover, the sensor device 1a according to the first embodiment can reduce the offset of the bit amplifier circuit 20a from the detection signal because the subtraction circuit 50 generates the difference between the reference signal and the detection signal. Accordingly, the sensor device 1a according to the first embodiment can further improve the detection accuracy.

Meanwhile, when the bit amplifier circuit 20a is set to function as the capacitive amplifier to output the detection signal, accuracy of an amplification factor of the detection signal depends on capacitance accuracy of the capacitor 21 and the capacitor 22. When a capacitor is formed in the standard semiconductor process, since the processing accuracy increases as the capacitance of a capacitor increases, the capacitance accuracy becomes easier to increase as a capacitance of the capacitor (for example, size of the capacitor) becomes larger. Accordingly, in order to increase the accuracy of the amplification factor of the detection signal output by the bit amplifier circuit 20a, it is preferred that the capacitor 21 and the capacitor 22 have relatively large capacitances.

Moreover, switching noise generated by the switching of the first changeover switch SW2 (for example, noise generated by charge injection) enters the capacitor 22 or the like to be absorbed thereby. Accordingly, also for the purpose of reducing effects of the switching noise on detection accuracy, it is preferred that the capacitor 21 and the capacitor 22 have the relatively large capacitances.

Here, the sensor device 1a according to the first embodiment sets the operational amplifier 23 to function as the voltage follower to obtain the reference signal, and generates the difference between the reference signal and the detection signal to reduce the offset of the bit amplifier circuit 20a.

In general, when the operational amplifier 23 is set to function as the voltage follower, in a case where the capacitance of the capacitor 21 is relatively large, phase margin of the operational amplifier 23 becomes smaller as compared to a case where the capacitance of the capacitor 21 is relatively small, and stable amplification may become difficult.

In other words, there arises an incompatible relationship in which in order to increase the accuracy of the amplification factor of the detection signal, it is preferred that the capacitor 21 have the relatively large capacitance, and in order to increase the phase margin of the operational amplifier 23, it is preferred that the capacitor 21 have a relatively small capacitance.

The sensor device 1a according to the first embodiment disconnects the capacitor 21 from the operational amplifier 23 when the operational amplifier 23 is set to function as the voltage follower. Therefore, according to the sensor device 1 a of the first embodiment, even when the capacitor 21 has the relatively large capacitance, the reduction in phase margin in the case where the operational amplifier 23 functions as the voltage follower can be suppressed.

Moreover, when the voltage of the detection electrode 11 is reset to the reference potential Vreset, it is preferred that the voltage of the capacitor 21 is also reset to the reference potential Vreset. If a configuration in which the capacitor 21 is not disconnected from the operational amplifier 23 is adopted here, when the voltage of the detection electrode 11 is reset to the reference potential Vreset, the capacitor 21 is also reset to the reference potential Vreset via the operational amplifier 23. However, in the sensor device 1a according to the first embodiment, since the capacitor 21 is disconnected from the operational amplifier 23 as described above in a period in which the voltage of the detection electrode 11 is reset to the reference potential Vreset, resetting of the voltage of the capacitor 21 via the operational amplifier 23 cannot be expected.

Here, in the sensor device 1a according to the first embodiment, the second reset switch SW4 resets the capacitor 21 to the reference potential Vreset in the period in which the capacitor 21 is disconnected from the operational amplifier 23. According to the sensor device 1a of the first embodiment, in the case where the operational amplifier 23 functions as the voltage follower, the suppression of the reduction in phase margin and the resetting of the capacitor 21 to the reference potential Vreset can thus both be achieved.

Moreover, in the first embodiment, the bit amplifier circuit 20a is a non-inverting amplifier circuit having the operational amplifier 23 (operational amplifier) which has the capacitor 22 connected between the output terminal and the inverting input terminal thereof has the capacitor 21 connected between the inverting input terminal and a GND line (reference potential line), and has the detection electrode 11 connected to the non-inverting input terminal thereof. The subtraction circuit 50 generates the differential signal obtained by subtracting the reference signal from the detection signal.

As a result, the sensor device 1a according to the first embodiment can amplify the voltage generated in the detection electrode 11 while reducing the offset with a simple configuration.

Moreover, in the first embodiment, the sampling circuit 30a holds the reference signal after the voltage of the detection electrode 11 is reset to the reference potential Vreset by the reset switch SW1, and the bit amplifier circuit 20a is set to function as the voltage follower by the first changeover switch SW2, and further a state in which the voltage of the detection electrode 11 is reset to the reference potential Vreset is released by the reset switch SW1, and the function as the voltage follower is released by the first changeover switch SW2. Moreover, the sampling circuit 30a holds the detection signal after the function as the voltage follower is released by the first changeover switch SW2, and the predetermined period elapses (period TR1 elapses) since the application of the predetermined voltage V1 to the external electrode 2.

As a result, the sampling circuit 30a holds the reference signal containing switching noise of the reset switch SW1 and the first changeover switch SW2. The sensor device 1a according to the first embodiment can thus reduce the offset as well as the switching noise of the reset switch SW1 and the first changeover switch SW2 with the difference between the detection signal and the reference signal.

Moreover, the sensor device 1a according to the first embodiment includes the timing control circuit 70a. The timing control circuit 70a performs the following timing control (A) to (C).

(A) Resetting the voltage of the detection electrode 11 to the reference potential Vreset by the reset switch SW1. Breaking the connection between the capacitor 21 and the inverting input terminal of the operational amplifier 23 by the second changeover switch SW3. Resetting the voltage of the capacitor 21 to the reference potential Vreset by the second reset switch SW4. Setting the bit amplifier circuit 20a to function as the voltage follower by the first changeover switch SW2.

In other words, breaking the connection between the capacitor 21 and the inverting input terminal of the operational amplifier 23 when the bit amplifier circuit 20a functions as the voltage follower. Moreover, resetting the voltage of the capacitor 21 to the reference potential Vreset when the capacitor 21 is disconnected from the operational amplifier 23.

(B) Releasing, by the reset switch SW1, from a state in which the voltage of the detection electrode 11 is reset to the reference potential Vreset. Releasing, by the second reset switch SW4, from a state in which the voltage of the capacitor 21 is reset to the reference potential Vreset. Making the connection between the capacitor 21 and the inverting input terminal of the operational amplifier 23 by the second changeover switch SW3. Holding the reference signal in the sampling circuit 30a after the function as the voltage follower is released by the first changeover switch SW2.

(C) Holding the detection signal by the sampling circuit 30a after the function as the voltage follower is released by the first changeover switch SW2, the connection between the capacitor 21 and the inverting input terminal of the operational amplifier 23 is made by the second changeover switch SW3, and the predetermined period TR1 elapses since the application of the predetermined voltage to the external electrode 2.

As a result, the sensor device 1a according to the first embodiment can reduce the offset as well as the switching noise of the reset switch SW1 and the first changeover switch SW2 as described above with the difference between the detection signal and the reference signal. Moreover, the sensor device 1a according to the first embodiment includes the timing control circuit 70a, and hence it is not required to externally perform complicated timing control.

Moreover, in the sensor device 1a according to the first embodiment, the magnitude of parasitic capacitance of the first changeover switch SW2 and the magnitude of parasitic capacitance of the second changeover switch SW3 are associated with each other. In general, when a semiconductor switch is turned from an ON state to an OFF state, electric charges flow out of the parasitic capacitance to generate the switching noise. Moreover, when the semiconductor switch is turned from the OFF state to the ON state, the electric charges flow into the parasitic capacitance to generate the switching noise. The amount of electric charges that flow in or out by the switching of the switch, that is, the magnitude of the switching noise, depends on the magnitude of parasitic capacitance of the semiconductor switch.

Meanwhile, the first changeover switch SW2 and the second changeover switch SW3 in the first embodiment are switched to opposite states from each other. Specifically, when the first changeover switch SW2 is turned off, the second changeover switch SW3 is turned on. In this case, the electric charges that flow as the switching noise out of the parasitic capacitance of the first changeover switch SW2 are accumulated in the capacitor 22, for example. The electric charges accumulated in the capacitor 22 flow into the parasitic capacitance of the second changeover switch SW3 when the second changeover switch SW3 is turned on. Here, in the sensor device 1a according to the first embodiment, the magnitude of parasitic capacitance of the first changeover switch SW2 and the magnitude of parasitic capacitance of the second changeover switch SW3 are associated with each other. For example, when the magnitude of parasitic capacitance of the first changeover switch SW2 and the magnitude of parasitic capacitance of the second changeover switch SW3 are equal to each other, the amount of electric charges that flow as the switching noise out of the parasitic capacitance of one switch and the amount of electric charges that flow into the parasitic capacitance of the other switch are equal to each other. Accordingly, in the sensor device 1a according to the first embodiment, it is possible to reduce accumulation of electric charges of the switching noise generated by the first changeover switch SW2 and the second changeover switch SW3, for example, in the capacitor 22.

Second Embodiment

Next, a sensor device 1b according to a second embodiment of the present invention is described with reference to the accompanying drawings.

In the second embodiment, a modification example of the bit amplifier circuit 20a according to the first embodiment is described.

Figure 3:
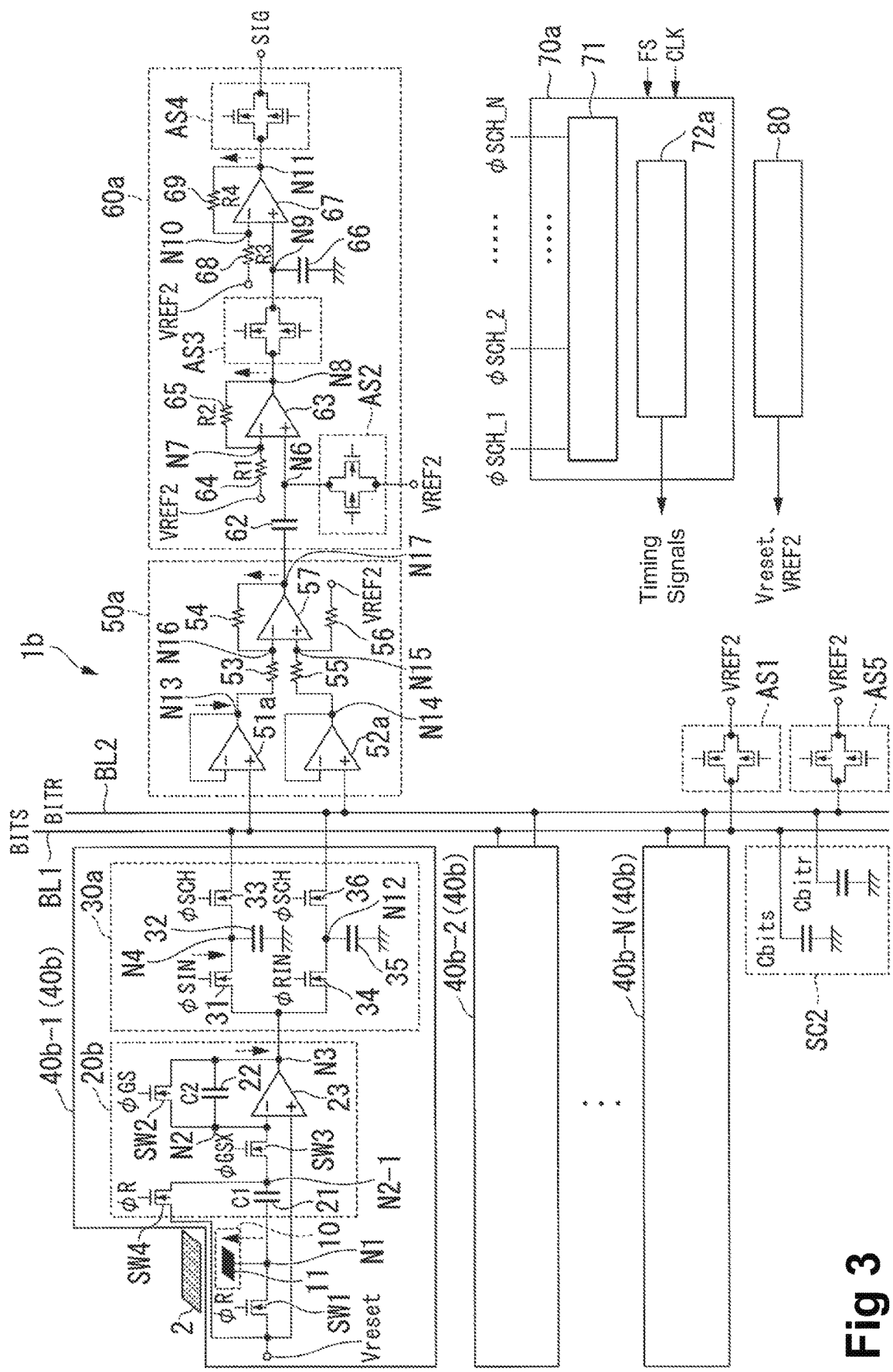
FIG. 3 is a block diagram for illustrating an example of a sensor device according to a second embodiment of the present invention.

FIG. 3 is a block diagram for illustrating an example of the sensor device 1b according to the second embodiment.

As illustrated in FIG. 3, the sensor device 1b includes the external electrode 2, pixel blocks (40b-1, 40b-2, . . . , 40b-N), a subtraction circuit 50a, the output processing circuit 60a, the timing control circuit 70a, and the reference voltage generation circuit 80.

In FIG. 3, the same components as those of the first embodiment illustrated in FIG. 1 are denoted by the same reference symbols, and a description thereof is omitted.

Moreover, in the second embodiment, the pixel blocks (40b-1, 40b-2, . . . , 40b-N) have the same configuration, and are described as the pixel block(s) 40b when any one of the pixel blocks included in the sensor device 1b is referred to, or when the pixel blocks are not particularly distinguished from one another.

The pixel block 40b is a block detects the electric field (thickness) of a pixel corresponding to one pixel, and includes the detection electrode 11, a bit amplifier circuit 20b, the sampling circuit 30a, and the reset switch SW1.

As with the bit amplifier circuit 20a in the first embodiment described above, the bit amplifier circuit 20b (one example of a capacitive amplifier circuit) detects a voltage generated in the detection electrode 11, and outputs a detection signal obtained by amplifying, based on a capacitance ratio between the capacitor 21 and the capacitor 22, the voltage generated in the detection electrode 11. The bit amplifier circuit 20b has the capacitor 21, the capacitor 22, the operational amplifier 23, the first changeover switch SW2, the second changeover switch SW3, and the second reset switch SW4. The bit amplifier circuit 20b is an inverting amplifier circuit having the operational amplifier 23 which has the capacitor 22 connected between an output terminal and an inverting input terminal thereof has the capacitor 21 connected between the inverting input terminal and the detection electrode 11 and has a Vreset signal line (reference potential line) connected to a non-inverting input terminal thereof. Here, the bit amplifier circuit 20b (operational amplifier 23) outputs the detection signal in a negative direction as an inverted signal.

The operational amplifier 23 has the inverting input terminal connected to a node N1 via the capacitor 21, and the non-inverting input terminal connected to the Vreset signal line.

The subtraction circuit 50a generates a difference between a reference signal and the detection signal which are held by the sampling circuit 30a. The subtraction circuit 50a generates a differential signal obtained by subtracting the detection signal from the reference signal. The subtraction circuit 50a has operational amplifiers (51a, 52a, and 57) and resistors (53 to 56).

The operational amplifier 51a has a non-inverting input terminal connected to a common signal line BL1, and an output terminal (node N13) connected to an inverting input terminal thereof.

The operational amplifier 52a has a non-inverting input terminal connected to a common signal line BL2, and an output terminal (node N14) connected to an inverting input terminal thereof.

The resistor 53 to the resistor 56 and the operational amplifier 57 form the subtraction circuit which subtracts the detection signal from the reference signal. The operational amplifier 57 outputs, to an output terminal (node N17), the differential signal obtained by subtracting the detection signal acquired via the common signal line BL1 from the reference signal acquired via the common signal line BL2 as the detection signal from which an offset of the bit amplifier circuit 20b is removed.

Operation of the sensor device 1b according to the second embodiment is similar to that in the first embodiment except that the bit amplifier circuit 20b is the inverting amplifier circuit, and that the subtraction circuit 50a subtracts the detection signal from the reference signal, and hence a description thereof is omitted here.

As described above, the sensor device 1b according to the second embodiment includes the detection electrode 11, the bit amplifier circuit 20b (capacitive amplifier circuit), the reset switch SW1, the first changeover switch SW2, the second changeover switch SW3, the second reset switch SW4, the sampling circuit 30a, and the subtraction circuit 50a.

As a result, the sensor device 1b according to the second embodiment can provide effects similar to those of the first embodiment, reduce effects of noise, and improve detection accuracy.

Moreover, the sensor device 1b according to the second embodiment can reduce the offset of the bit amplifier circuit 20b from the detection signal because the subtraction circuit 50a generates the difference between the reference signal and the detection signal. The sensor device 1b according to the third embodiment can thus further improve the detection accuracy.

Moreover, in the second embodiment, the bit amplifier circuit 20b is an inverting amplifier circuit including the operational amplifier 23 which has the capacitor 22 connected between the output terminal and the inverting input terminal thereof, the capacitor 21 connected between the inverting input terminal and the detection electrode 11, and the Vreset signal line (reference potential line) connected to the non-inverting input terminal thereof. The subtraction circuit 50a generates the differential signal obtained by subtracting the detection signal from the reference signal.

As a result, the sensor device 1b according to the second embodiment can amplify the voltage generated in the detection electrode 11 while reducing the offset with a simple configuration.

The present invention is not limited to the embodiments described above, and can be modified without departing from the spirit of the present invention.

For example, in the embodiments described above, the example in which the timing control circuit 70a generates the various timing signals has been described. However, the present invention is not limited thereto, and some or all of the various timing signals generated by the timing control circuit 70a may be externally supplied.

Moreover, in the embodiments described above, the example in which the reference voltage generation circuit 80 generates the reference voltages, such as the reference potential Vreset and the reference potential VREF2, has been described. However, the present invention is not limited thereto, and some or all of the reference voltages generated by the reference voltage generation circuit 80 may be externally supplied.

Moreover, in the embodiments described above, there has been described the example in which the pixel blocks 40a (40b) detect the detection signals for all pixels at once, hold the detection signals in the sampling circuits 30a, and sequentially and serially output the detection signals, but the present invention is not limited thereto. The timing control circuit 70a may perform the timing control such that the pixel blocks 40a (40b) sequentially output the detection signal while detecting the detection signals one pixel (one bit) at a time, for example.

Moreover, in the embodiments described above, the example in which the output processing circuit 60a amplifies the detection signal in two stages has been described, but the present invention is not limited thereto. When a sufficient dynamic range can be secured with one-step amplification, for example, the output processing circuit 60a may amplify the detection signal in one stage.

Moreover, in the embodiments described above, the example in which the sensor device 1a (1b) is a line image sensor device has been described. However, the present invention is not limited thereto, and the sensor device 1a (1b) may be a two-dimensional image sensor device.

Moreover, in the first embodiment described above, the example in which the bit amplifier circuit 20a is formed of the non-inverting amplifier circuit has been described, but may be formed of the inverting amplifier circuit as in the second embodiment.

Moreover, the timing control circuit 70a described above may have a computer system therein. At this time, the above-mentioned processing step of detecting the output of the detection electrode 11 is stored in a form of a program in a computer-readable storage medium, and the above-mentioned processing is performed by reading and executing the program by a computer. The "computer-readable storage medium" as used herein refers to a magnetic disk, a magneto-optical disk, a CD-ROM, a DVD-ROM, or a semiconductor memory, for example. Moreover, the computer program may be distributed to the computer through a communication line, and the computer that has received the distributed program may execute the program.

What is claimed is:

1. A sensor device, comprising:
a detection electrode opposing an external electrode to which a predetermined voltage is applied, and configured to generate a voltage corresponding to a change in electrostatic capacitance;
a capacitive amplifier circuit having an operational amplifier, a first capacitor, and a second capacitor, the first capacitor connected in series to the second capacitor, the second capacitor connected between an output terminal and an inverting input terminal of the operational amplifier, and the capacitive amplifier circuit being configured to detect the voltage generated in the detection electrode, and output a detection signal obtained by amplifying the voltage generated in the detection electrode based on a capacitance ratio between the first capacitor and the second capacitor;
a reset switch configured to reset the voltage of the detection electrode to a reference potential;
a changeover switch configured to switch the capacitive amplifier circuit between functioning as a capacitive amplifier and functioning as a voltage follower by establishing a short circuit between the output terminal and the inverting input terminal;
a second changeover switch configured to disconnect the first capacitor from the capacitive amplifier circuit for the capacitive amplifier circuit to function as the voltage follower; and
a second reset switch configured to reset a voltage of the first capacitor to the reference potential according to disconnection of the first capacitor from the capacitive amplifier circuit.

2. A sensor device according to claim 1, wherein a magnitude of parasitic capacitance of the changeover switch and a magnitude of parasitic capacitance of the second changeover switch are associated with each other.

3. A sensor device according to claim 2, further comprising:
a sampling circuit configured to sample and hold a reference signal and the detection signal respectively, the reference signal being an output signal from the capacitive amplifier circuit before the predetermined voltage is applied to the external electrode, the detection signal being under a condition in which the predetermined voltage is applied to the external electrode, after the voltage of the detection electrode and the voltage of the first capacitor are reset to the reference potential by the reset switch and the second reset switch respectively, and the first capacitor is disconnected from the capacitive amplifier circuit by the second changeover switch and the capacitive amplifier circuit is set to function as the voltage follower by the changeover switch; and a subtraction circuit configured to generate a difference between the reference signal and the detection signal held by the sampling circuit.

4. A sensor device according to claim 1, further comprising:

a sampling circuit configured to sample and hold a reference signal and the detection signal respectively, the reference signal being an output signal from the capacitive amplifier circuit before the predetermined voltage is applied to the external electrode, the detection signal being under a condition in which the predetermined voltage is applied to the external electrode, after the voltage of the detection electrode and the voltage of the first capacitor are reset to the reference potential by the reset switch and the second reset switch respectively, and the first capacitor is disconnected from the capacitive amplifier circuit by the second changeover switch and the capacitive amplifier circuit is set to function as the voltage follower by the changeover switch; and a subtraction circuit configured to generate a difference between the reference signal and the detection signal held in the sampling circuit.

5. A sensor device according to claim 4,
wherein the capacitive amplifier circuit includes a non-inverting amplifier circuit which has the first capacitor connected between the inverting input terminal and a reference potential line and has the detection electrode connected to a non-inverting input terminal of the operational amplifier and
wherein the subtraction circuit is configured to generate a differential signal obtained by subtracting the reference signal from the detection signal.

6. A sensor device according to claim 4,
wherein the capacitive amplifier circuit includes an inverting amplifier circuit which has the first capacitor connected between the inverting input terminal and the detection electrode and has a reference potential line connected to a non-inverting input terminal of the operational amplifier and
wherein the subtraction circuit is configured to generate a differential signal obtained by subtracting the detection signal from the reference signal.

7. A sensor device according to claim 6, wherein the sampling circuit is configured to:

hold the reference signal after the voltage of the detection electrode and the voltage of the first capacitor are reset to the reference potential by the reset switch and the second reset switch, respectively, the first capacitor is disconnected from the capacitive amplifier circuit by the second changeover switch, and the capacitive amplifier circuit is set to function as the voltage follower by the changeover switch, and further after a state in which the voltage of the detection electrode is reset to the reference potential is released by the reset switch, the function as the voltage follower is released by the changeover switch, and the first capacitor is connected to the capacitive amplifier circuit by the second changeover switch; and hold the detection signal after the function as the voltage follower is released by the changeover switch, the first capacitor is connected to the capacitive amplifier circuit by the second changeover switch, and after an elapse of a predetermined period since the application of the predetermined voltage to the external electrode.

8. A sensor device according to claim 7, further comprising a timing control circuit configured to:

hold the reference signal in the sampling circuit after resetting the voltage of the detection electrode and the voltage of the first capacitor to the reference potential by the reset switch and the second reset switch, respectively, disconnecting the first capacitor from the capacitive amplifier circuit by the second changeover switch, and resetting the capacitive amplifier circuit to function as the voltage follower by the changeover switch, further releasing a state in which the voltage of the detection electrode is reset to the reference potential by the reset switch, releasing the function as the voltage follower by the changeover switch, and connecting the first capacitor to the capacitive amplifier circuit by the second changeover switch; and hold the detection signal by the sampling circuit after releasing the function as the voltage follower by the changeover switch, and after an elapse of a predetermined period since the application of the predetermined voltage to the external electrode.

9. A sensor device according to claim 6, further comprising a timing control circuit configured to:

hold the reference signal in the sampling circuit after resetting the voltage of the detection electrode and the voltage of the first capacitor to the reference potential by the reset switch and the second reset switch, respectively, disconnecting the first capacitor from the capacitive amplifier circuit by the second changeover switch, and setting the capacitive amplifier circuit to function as the voltage follower by the changeover switch, further releasing a state in which the voltage of the detection electrode is reset to the reference potential by the reset switch, releasing the function as the voltage follower by the changeover switch, and connecting the first capacitor to the capacitive amplifier circuit by the second changeover switch; and hold the detection signal in the sampling circuit after releasing the function as the voltage follower by the changeover switch, and after an elapse of a predetermined period since the application of the predetermined voltage to the external electrode.

10. A sensor device, comprising:
a plurality of detection electrodes arranged in line; and
a plurality of capacitive amplifier circuits respectively corresponding to the plurality of detection electrodes, each one of the plurality of detection electrodes and each one of the plurality of capacitive amplifiers forming the senor device of claim 6.

11. A sensor device, comprising:
a plurality of detection electrodes arranged in line; and
a plurality of capacitive amplifier circuits respectively corresponding to the plurality of detection electrodes, each one of the plurality of detection electrodes and each one of the plurality of capacitive amplifiers forming the senor device of claim 4.

12. A sensor device, comprising:
a plurality of detection electrodes arranged in line; and
a plurality of capacitive amplifier circuits respectively corresponding to the plurality of detection electrodes, each one of the plurality of detection electrodes and each one of the plurality of capacitive amplifiers forming the senor device of claim 1.

* * * * *